United States Patent
Rhoden

(10) Patent No.: US 10,495,740 B2
(45) Date of Patent: Dec. 3, 2019

(54) SHORT RANGE ULTRASONIC MEASUREMENT

(71) Applicant: Hamilton Sundstrand Corporation, Charlotte, NC (US)

(72) Inventor: William E. Rhoden, Glastonbury, CT (US)

(73) Assignee: Hamilton Sundstrand Corporation, Charlotte, NC (US)

( * ) Notice: Subject to any disclaimer, the term of this patent is extended or adjusted under 35 U.S.C. 154(b) by 262 days.

(21) Appl. No.: 15/681,520

(22) Filed: Aug. 21, 2017

(65) Prior Publication Data

US 2019/0056485 A1   Feb. 21, 2019

(51) Int. Cl.
| | |
|---|---|
| *G01S 15/08* | (2006.01) |
| *G01S 7/52* | (2006.01) |
| *G01N 29/30* | (2006.01) |
| *G01B 17/00* | (2006.01) |

(52) U.S. Cl.
CPC .......... *G01S 7/52004* (2013.01); *G01B 17/00* (2013.01); *G01N 29/30* (2013.01); *G01S 15/08* (2013.01); *G01N 2291/105* (2013.01); *G01N 2291/263* (2013.01); *G01S 2007/52014* (2013.01)

(58) Field of Classification Search
CPC ....... G01S 7/52004; G01S 2007/52014; G01B 17/00; G01N 29/30; G01N 2291/105; G01N 2291/263

See application file for complete search history.

(56) References Cited

U.S. PATENT DOCUMENTS

| | | | | |
|---|---|---|---|---|
| 4,008,455 A | * | 2/1977 | Pedersen | G01S 7/52004 376/245 |
| 4,543,649 A | | 9/1985 | Head et al. | |
| 4,769,793 A | * | 9/1988 | Kniest | G01H 11/06 367/151 |
| 4,938,054 A | * | 7/1990 | Dye | G01B 17/00 73/1.21 |
| 4,964,104 A | * | 10/1990 | Capurka | B60G 17/01933 367/99 |
| 5,095,754 A | * | 3/1992 | Hsu | B64D 15/20 340/962 |
| 5,917,776 A | | 6/1999 | Foreman | |

(Continued)

FOREIGN PATENT DOCUMENTS

| | | |
|---|---|---|
| WO | 90/07721 A1 | 7/1990 |
| WO | 2005/003571 A1 | 1/2005 |

OTHER PUBLICATIONS

European Search Report for EP Application No. 18189692.9 dated Jan. 2, 2019.

*Primary Examiner* — David J Bolduc
(74) *Attorney, Agent, or Firm* — Carlson, Gaskey & Olds, P.C.

(57) ABSTRACT

A system has an actuator with a first surface and a second surface, the first surface being offset a step dimension from the second surface. A sensor is configured to measure a distance between the sensor and both the first surface and the second surface via a signal received by the sensor after having reflected off the first surface or the second surface. The step dimension is greater than a minimum dimension, which is defined in view of a medium through which the actuator moves and a frequency of the signal.

13 Claims, 2 Drawing Sheets

(56) References Cited

U.S. PATENT DOCUMENTS

| | | | | |
|---|---|---|---|---|
| 6,119,579 | A * | 9/2000 | Pawelski | B60G 17/01933 92/5 R |
| 6,142,059 | A * | 11/2000 | Chan | F15B 15/2869 91/361 |
| 6,435,031 | B1 * | 8/2002 | Nagai | G01D 5/00 310/321 |
| 8,171,771 | B2 | 5/2012 | Hain et al. | |
| 9,151,840 | B2 | 10/2015 | Koudar | |
| 9,163,471 | B2 * | 10/2015 | Coonrod | E21B 33/0355 |
| 9,187,974 | B2 * | 11/2015 | Coonrod | E21B 33/061 |
| 9,223,023 | B2 | 12/2015 | Zhou et al. | |
| 9,804,039 | B2 * | 10/2017 | Reyes, III | E21B 34/16 |
| 2005/0223808 | A1 * | 10/2005 | Myers | G01N 29/024 73/629 |
| 2010/0288036 | A1 * | 11/2010 | Volkwein | G01B 17/00 73/114.29 |
| 2018/0074020 | A1 * | 3/2018 | Paradise | G01N 29/07 |

\* cited by examiner

SHORT RANGE ULTRASONIC MEASUREMENT

BACKGROUND OF THE INVENTION

This application relates to an apparatus and a method for measuring a position of a moving component within a very small difference from an end of travel position.

Modern systems are becoming more and more precise. One such system is an actuator for moving components. Example components could be any number of components on an aircraft application. So-called linear variable displacement transducers (LVDTs) monitor a position of a surface in the actuator to provide the feedback to a control of that position. The control may control a motor for the actuator such that the actuator can be assured to move the component to a desired position.

One such LVDT utilizes ultrasonic waves bounced off a surface on a component in the actuator. Such systems provide very good accuracy for position feedback.

However, it is known that when the distance to the target surface becomes very small, the ultrasonic measuring device can have signal interference. In particular, the sensor generally works by sending an outgoing signal which reflects off of a target surface and back to the sensor. The time of this travel is monitored to provide the position feedback.

When the distance becomes less than a minimum distance, the outgoing signal can interfere with the incoming reflected signal.

The minimum difference varies by the frequency of the signal and the speed of sound in the medium through which the signal is traveling. As one example, there is a five millimeter minimum distance from a target utilizing a 2.5 megahertz transducer in a water medium.

SUMMARY OF THE INVENTION

As shown in FIG. 1A, a system has an actuator with a first surface and a second surface, the first surface being offset a step dimension from the second surface. A sensor is configured to measure a distance between the sensor and both the first surface and the second surface via a signal received by the sensor after having reflected off the first surface or the second surface. The step dimension is greater than a minimum dimension, which is defined in view of a medium through which the actuator moves and a frequency of the signal.

A method is also disclosed.

These and other features may be best understood from the following drawings and specification.

DETAILED DESCRIPTION

Figure 1A:
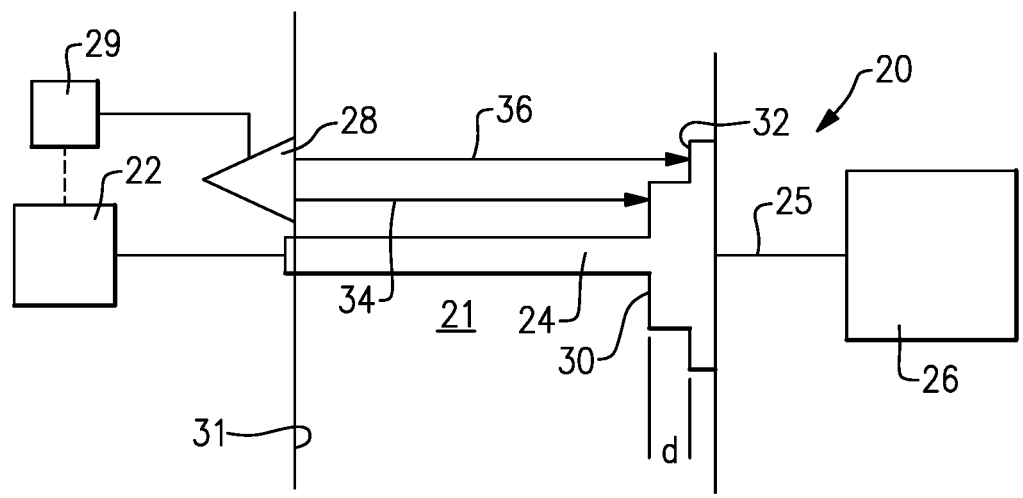
FIG. 1A schematically shows an actuator system.

A system 20 includes a motor 22 for moving an actuator 24 to, in turn, move a shaft 25 to change a location of a component 26. The component 26 may be a moving system on an aircraft. It should be understood that this system may include linear movement, pivoting movement, rotating movement, or any number of combinations of such types of movement. This disclosure is not limited to the actuation system, nor to the component 26 being controlled.

A sensor 28, which may be a linear variable displacement transducer and, in particular, utilizing ultrasonic signals is positioned to monitor the location of the moving actuator 24. As shown, a signal 34 reflects off of a surface 30 that will eventually be a stop surface or a surface closest to the sensor at an end of travel position.

The signal 34 reflects off the surface 30 and returns to the sensor. The actuator 24 is moving through a medium 21. In one application, the medium may be water. Of course, other fluids including fuel, air, oil, hydraulic fluid, a coolant or others may be used.

Figure 1B:
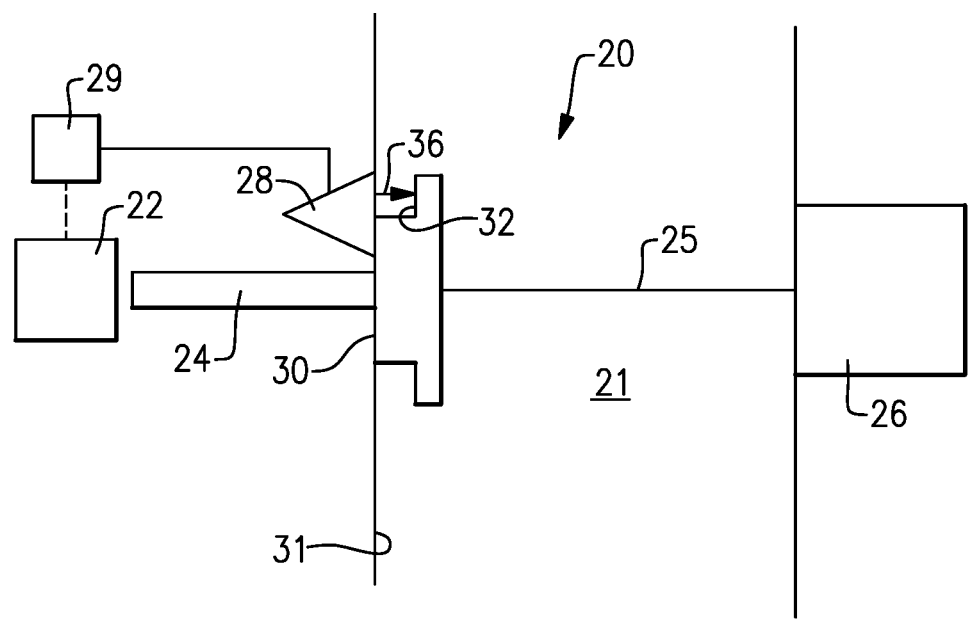
FIG. 1B shows an actuator system of FIG. 1A in a distinct location.

FIG. 1B shows an end of travel position where the surface 30 is now bottomed out against an end wall 31. As the actuator 24 and, in particular, surface 30 get very close to sensor 28, it will be move within a minimum distance for accurate measurement. As mentioned above, when the surface 30 is close to a sensor 28, there can be interference between the outgoing and the reflected signals.

As mentioned, in an application wherein a 2.5 megahertz transducer is operating in a water medium, the minimum distance might be 5 millimeters. Of course, this is but an example. Many other combinations would benefit from this disclosure.

Modern control systems need the ability to accurately measure the position to a fine degree (in this example, less than five millimeters). As such, movement within this minimum distance would be desirably sensed.

Thus, a step surface 32 is also formed spaced from the surface 30 by a step dimension. The step surface 32 is generally selected to be at least beyond the minimum distance from the sensor 28 relative to the surface 30. As the component 24 approaches the FIG. 1B position, the control 29 switches the sensor 28 to measuring the distance to both surfaces 30 and 32. Alternatively, the control 29 can simply switch the sensor from measuring to surface 30 to measuring to surface 32.

The control 29 is preferably programmed to ignore unstable signals, such as may be expected from the surface 30 as it moves within this minimum distance.

Also, once a distance d between the surfaces 30 and 32 and measured parallel to an axis of movement of the component 24, is known, sensing to the surfaces 30 and 32 will allow very fine calibration of the operation of the sensor.

In particular, in a calibration mode, the sensor can send a signal off both surfaces 30 and 32, and then determine an apparent distance to the two surfaces. That distance should vary by the distance d. If it does, then a decision can be made by the control that the sensor is well calibrated. On the other hand, should the apparent distance differ from d by more than a pre-determined amount, the control 29 may determine that calibration is in order.

Figure 2:
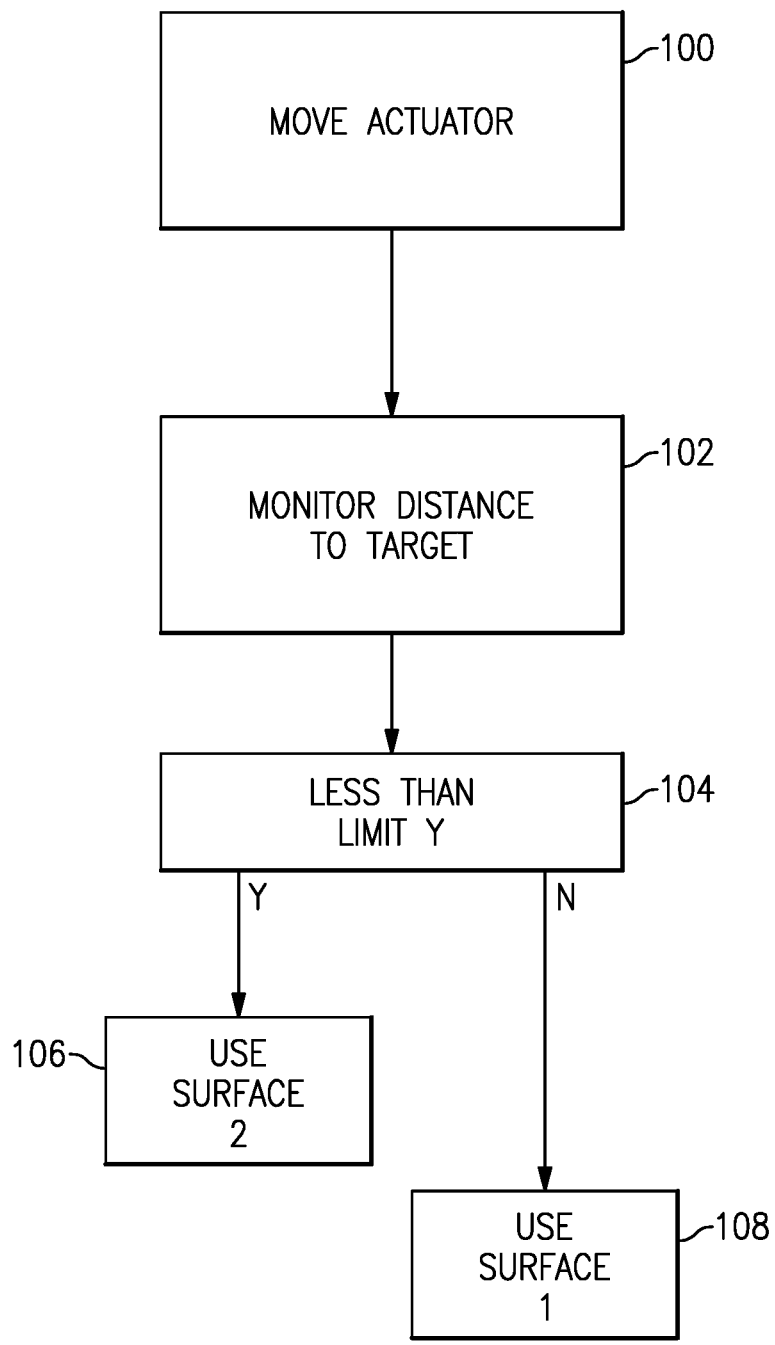
FIG. 2 is a flowchart.

While the system is disclosed switching between the two surfaces, in at least a broadest sense, a method and apparatus might simply sense to a target surface 32 that is far enough away from the sensor 28 at an end of travel position, that the minimum distance does not become a problem FIG. 2 shows a flowchart having a step 100 of moving an actuator. A sensor monitors a distance to a target on the actuator. At 104, the distance is compared to a limit. In general, at 106, if the distance is less than a limit, then the control switch is to utilize a secondary surface at 106. On the other hand, if the distance is not less than the limit then the primary surface is utilized at step 108.

As mentioned above, in one embodiment, at least during a portion of operation, the distance to both surfaces is monitored.

A method of operating a system includes the steps of moving an actuator and sensing a distance to a first surface on the moving actuator. The sensor is operable to utilize the sensed distance as position feedback for a component moved by the actuator. The first surface is spaced from the sensor by a distance that is less than a minimum distance in an end of travel position. The said minimum distance is defined in view of a medium through which the moving actuator moves, and a frequency of a signal from the sensor. A signal is sent off of a second surface on the moving actuator that will be spaced from the sensor by a distance greater than the minimum distance when the actuator is in said end of travel position.

Although an embodiment of this invention has been disclosed, a worker of ordinary skill in this art would recognize that certain modifications would come within the scope of this invention. For that reason, the following claims should be studied to determine the true scope and content of this invention.

The invention claimed is:

1. A system comprising:
   an actuator having a first surface and a second surface, the first surface being offset a step distance from the second surface;
   a sensor configured to measure a distance between the sensor and both the first surface and the second surface via a signal received by the sensor after having reflected off the first surface or the second surface, wherein the step distance is greater than a minimum distance, the minimum distance being defined in view of a medium through which said actuator moves and a frequency of the signal; and
   wherein the first surface is positionable nearer to the sensor than the minimum dimension when the actuator reaches an end of travel position.

2. The system as set forth in claim 1, wherein said sensor initially directing a signal to reflect off of said first surface for a period of time, and sending a signal to reflect off of said second surface at least when said first surface approaches the minimum distance from said sensor.

3. The system as set forth in claim 2, wherein said sensor sends a signal to reflect off of both said first and said second surfaces at least for a period of time as said first surface approaches said minimum distance.

4. The system as set forth in claim 3, wherein said medium is water.

5. The system as set forth in claim 4, wherein said actuator moves a component associated with aircraft.

6. The system as set forth in claim 1, wherein a control for said system being programmed to know the step distance, and to compare an apparent difference sensed between distances to said first and second surfaces to said step distance, and determine whether calibration is in order based upon this comparison.

7. The system as set forth in claim 1, wherein said actuator moves a component associated with aircraft.

8. A method of operating a system comprising the steps of:
   moving an actuator having a first surface and a second surface, the first surface offset from the second surface by a step distance;
   sensing a distance between a sensor and both the first surface and the second surface via a signal received by the sensor after having reflected off the first surface or the second surface, wherein the step distance is greater than a minimum distance, the minimum distance being defined in view of a medium through which said actuator moves and a frequency of the signal; and
   wherein the first surface is positionable nearer to the sensor than the minimum dimension when the actuator reaches an end of travel position.

9. The method as set forth in claim 8, wherein said sensor initially directing a signal to reflect off of said first surface for a period of time, and sending a signal to reflect off of said second surface at least when said first surface approaches the minimum distance from said sensor.

10. The method as set forth in claim 9, wherein said sensor sends a signal to reflect off of both said first and said second surfaces at least for a period of time as said first surface approaches said minimum distance.

11. The method as set forth in claim 10, wherein said actuator moves a component associated with aircraft.

12. The method as set forth in claim 8, wherein a control for said system being programmed to know the step distance, and comparing an apparent difference sensed between distances to said first and second surfaces to said step distance, and determine whether calibration is in order based upon this comparison.

13. The method as set forth in claim 8, wherein said actuator moves a component associated with aircraft.

* * * * *